US012758478B2

(12) United States Patent
Hiban et al.

(10) Patent No.: US 12,758,478 B2
(45) Date of Patent: Oct. 13, 2026

(54) ESTER COMPRISING HYDRATABLE CONCENTRATED SURFACTANT COMPOSITION

(71) Applicant: Conopco, Inc., Englewood Cliffs, NJ (US)

(72) Inventors: Douglas John Hiban, Newtown, CT (US); Teanoosh Moaddel, Watertown, CT (US); Tirucherai Varahan Vasudevan, Bethany, CT (US); Thomas Alan Kwan, Sudbury, MA (US)

(73) Assignee: Conopco Inc., Hoboken, NJ (US)

( * ) Notice: Subject to any disclaimer, the term of this patent is extended or adjusted under 35 U.S.C. 154(b) by 377 days.

(21) Appl. No.: 18/572,036

(22) PCT Filed: Jun. 30, 2022

(86) PCT No.: PCT/EP2022/068162

§ 371 (c)(1),
(2) Date: Dec. 19, 2023

(87) PCT Pub. No.: WO2023/275299

PCT Pub. Date: Jan. 5, 2023

(65) Prior Publication Data

US 2024/0299274 A1 Sep. 12, 2024

(30) Foreign Application Priority Data

Jul. 2, 2021 (EP) .................................... 21183528

(51) Int. Cl.

| | |
|---|---|
| ***A61G 19/00*** | (2006.01) |
| ***A61K 8/34*** | (2006.01) |
| ***A61K 8/365*** | (2006.01) |
| ***A61K 8/368*** | (2006.01) |
| ***A61K 8/37*** | (2006.01) |
| ***A61K 8/44*** | (2006.01) |
| ***A61K 8/46*** | (2006.01) |
| ***A61K 8/67*** | (2006.01) |
| ***A61Q 19/10*** | (2006.01) |

(52) U.S. Cl.

CPC .............. *A61K 8/466* (2013.01); *A61K 8/347* (2013.01); *A61K 8/365* (2013.01); *A61K 8/368* (2013.01); *A61K 8/375* (2013.01); *A61K 8/442* (2013.01); *A61K 8/675* (2013.01); *A61Q 19/10* (2013.01)

(58) Field of Classification Search

CPC ........ A61K 8/466; A61K 8/347; A61K 8/365; A61K 8/368; A61K 8/375; A61K 8/442; A61K 8/675; A61K 2800/30; A61K 2800/48; A61K 2800/596; A61K 8/342; A61K 8/361; A61K 8/37; A61K 8/42; A61K 8/44; A61K 8/0295; A61Q 19/10; A61Q 5/02

USPC .......................................................... 510/159

See application file for complete search history.

(56) References Cited

U.S. PATENT DOCUMENTS

| | | | | |
|---|---|---|---|---|
| 5,009,814 | A | 4/1991 | Kelkenberg et al. | |
| 5,389,279 | A | 2/1995 | Au et al. | |
| 5,393,466 | A | 2/1995 | Ilardi et al. | |
| 2014/0121268 | A1* | 5/2014 | Guskey ................. | A61Q 19/10 514/517 |
| 2014/0162979 | A1 | 6/2014 | Sekhar et al. | |
| 2016/0000669 | A1 | 1/2016 | Hinman et al. | |
| 2018/0098923 | A1 | 4/2018 | Hutton, III | |
| 2018/0116937 | A1 | 5/2018 | Park et al. | |
| 2018/0280270 | A1 | 10/2018 | Rughani et al. | |
| 2019/0282480 | A1 | 9/2019 | Su et al. | |
| 2019/0314258 | A1 | 10/2019 | Laurent et al. | |
| 2019/0365622 | A1 | 12/2019 | Botto et al. | |
| 2020/0078284 | A1 | 3/2020 | Botto et al. | |

FOREIGN PATENT DOCUMENTS

| | | | |
|---|---|---|---|
| CN | 112957289 | 6/2021 | |
| EP | 2644185 | 10/2013 | |
| WO | WO9612468 | 5/1996 | |
| WO | WO9705857 | 2/1997 | |
| WO | WO2016172482 | 10/2016 | |
| WO | WO2019000394 | 1/2019 | |
| WO | WO 2019000394 A1 * | 1/2019 | ............. A61Q 19/10 |
| WO | WO2019008937 | 1/2019 | |
| WO | WO2019074993 | 4/2019 | |

OTHER PUBLICATIONS

Search Report in EP21183529.3; Jan. 27, 2022.
Search Report and Written Opinion in PCT/EP2022/068161; Oct. 31, 2022.
Cleansing Foam; Mintel, Record ID 8590653; 2021.
Kalia; Colloid Polymer Science; Nanofibrillated cellulose surface modification and potential applications; vol. 292; pp. 5-31; 2014.
Search Report and Written Opinion in PCT/EP2022/068162; Oct. 31, 2022; World Intellectual Property Org. (WIPO).

(Continued)

*Primary Examiner* — Eisa B Elhilo
(74) *Attorney, Agent, or Firm* — Edward A. Squillante, Jr.

(57) ABSTRACT

The invention is directed to a hydratable concentrated surfactant composition. The composition is pourable, easy to dilute, substantially free of sulfate and oil, comprises a $C_6$-$C_{14}$ acid, alcohol, amide or mixture thereof, anionic surfactant and an amphoteric surfactant, zwitterionic surfactant or both. The composition is in lamellar phase and thickens and transforms to an isotropic phase upon dilution. The composition comprises a mono-, di and/or tri-ester, can be used as a concentrate in small volumes and diluted as used and needed or can be diluted with water in refill packaging to ensure a reduction in plastic waste.

20 Claims, No Drawings

(56) References Cited

OTHER PUBLICATIONS

Search Report and Written Opinion in EP21183528.5; Jan. 27, 2022; European Patent Office (EPO).

* cited by examiner

ESTER COMPRISING HYDRATABLE CONCENTRATED SURFACTANT COMPOSITION

FIELD OF THE INVENTION

The present invention is directed to an ester comprising hydratable concentrated surfactant composition. The composition is pourable, substantially free of sulfate and oil, comprises a $C_6$-$C_{14}$ acid or an alcohol or amide derivative thereof, or mixture thereof, anionic surfactant, and an amphoteric surfactant, zwitterionic surfactant or both. The hydratable concentrated surfactant composition may optionally comprise a structurant, and the ester is preferably a mono-, di- or tri-ester or a mixture thereof.

BACKGROUND OF THE INVENTION

Liquid based cleansing compositions, such as shampoos and body washes, are common and enjoyed by many consumers. Such compositions typically have water as the predominant ingredient, and they are often sold in plastic bottles or tubes. The compositions are conventionally formulated to have a viscosity that is customary for consumer use and easy for evacuation from the package they are sold in.

It is often publicized that the world's oceans will soon have more plastic than fish. Given environmental concerns and the desire for consumers and conscious companies to do more for the planet, there is a strong desire to use less plastic when selling products, including consumer products. In view of this, efforts have been made to sell product in concentrate form, and therefore, ship product that comprises less water. The difficulty with concentrates is consumers often do not like adding additional water to the concentrate and further work, like stirring and shaking, to transform the concentrate into an end usable product. As to the hydrated product, common complaints include that the product is not homogeneous after adding water and/or of undesirable viscosity.

It is of increasing interest to develop a concentrate that is easy to pour and hydrate, results in a consumer product that is ready to use in under five (5) minutes and of very desirable characteristics, including viscosity. It is also desirable to develop a concentrate that is substantially free of sulfate and that is easy to use with a refill package to reduce plastic waste.

This invention, therefore, is directed to a hydratable concentrated composition that comprises a $C_6$-$C_{14}$ acid or an alcohol or amide derivative thereof, or mixture thereof, anionic surfactant, and an amphoteric surfactant, zwitterionic surfactant or both. The composition may further comprise an optional structurant, and especially, when the anionic surfactant used comprises less than 2.0% by weight isethionate. The composition is in lamellar phase, and unexpectedly, thickens and transforms to an isotropic phase upon dilution. The composition can be used as a concentrate that is diluted as needed or can be diluted with water in refill packaging to ensure a reduction in plastic waste. Furthermore, the composition of the present invention can be formulated at low pH to better accommodate acidic actives.

Additional information Efforts have been disclosed for making wash compositions. In U.S. patent application publication 2019/0314258 A1, rheofluidifying concentrated foaming compositions are described.

Further efforts have been disclosed for making wash compositions. In WO2019/074992A1 and WO2019/074993A1, sulfate free personal cleansing compositions with low inorganic salt are described.

Even other efforts have been disclosed for making wash compositions. In U.S. patent application publication 2018/098923 A1, personal care compositions substantially free of sulfated surfactants are described.

Still other efforts have been disclosed for making wash compositions. In U.S. patent application 2019/282480 A1, self-thickening cleansing compositions with N-acyl acidic amino acids or salts thereof and an amphoteric surfactant are described.

None of the additional information describes concentrated surfactant containing compositions as described and claimed in the present invention.

SUMMARY OF THE INVENTION

In a first aspect, the present invention is directed to a hydratable concentrated surfactant composition having a viscosity from 0.025 to 10 PaS (25 to 10,000 cps) (preferably from 0.025 to 7.5 PaS (25 to 7,500 cps), more preferably, from 0.25 to 3.5 PaS (250 to 3,500 cps)) wherein the composition thickens and increases in viscosity when diluted with water at a composition to water weight ratio from 1:1 to 1:10 (preferably 1:1 to 1:7, more preferably 1:1.5 to 1:6, most preferably 1:1.75 to 1:3) to produce an end use composition having a viscosity from 1 to 20 PaS (1,000 to 20,000 cps) (preferably 2 to 15 PaS (2,000 to 15,000 cps), even more preferably, 3 to 12 PaS (3,000 to 12,000 cps), and most preferably, 5 to 9 PaS (5,000 to 9,000 cps)), the composition comprises from 0.75 to 5.0% by weight of at least one of a mono-, di, or tri-ester or a mixture thereof, the ester having a weight percent of oxygen from 12 to 45.

In a second aspect, the present invention is directed to the hydratable concentrated surfactant composition of the first aspect of the invention wherein the composition transforms from lamellar to isotropic form (i.e., microstructure) upon dilution.

In a third aspect, the present invention is directed to the hydratable concentrated surfactant composition having a viscosity from 0.025 to 10 PaS (25 to 10,000 cps) wherein the composition is suitable to be diluted with water at a composition to water weight ratio from 1:1 to 1:10 to produce an end use composition having a viscosity from 1 to 20 PaS (1,000 to 20,000 cps) and further wherein the hydratable composition comprises:

a) an anionic surfactant;
b) an amphoteric and/or zwitterionic surfactant;
c) a $C_6$-$C_{14}$ acid, amide and/or alcohol;
d) from 30 to 85% by weight water; and
e) from 0.5 to 5% by weight of at least one of a mono-, di- or tri-ester, the ester having a weight percent of oxygen from 12 to 45 and the end use composition having a viscosity that is greater than the viscosity of the hydratable concentrated surfactant composition.

In a fourth aspect, the invention is directed to a hydratable concentrated surfactant composition comprising:

a) an anionic surfactant;
b) an amphoteric and/or zwitterionic surfactant;
c) a $C_6$-$C_{14}$ acid, amide and/or alcohol;
d) from 30 to 85% by weight water; and
f) from 0.5 to 5% by weight of hexyl salicylate, hexyl acetate, diethylhexyl malate, dioctyl maleate, diisopropyl adipate, glyceryl caprylate, glycerin triacetate, diethyl hexyl sebacate or a mixture thereof or a mixture thereof.

In a fifth aspect, the invention is directed to an end use composition made by diluting at least one of the hydratable concentrated surfactant compositions of the first four aspects of the invention wherein the end use composition produced has a viscosity that is greater than the viscosity of the hydratable concentrated surfactant composition it is prepared from.

In a sixth aspect, the invention is directed to the use of the end use composition of the fifth aspect of the invention to cosmetically treat skin.

In a seventh aspect, the invention is directed to the use of a of a mono-, di- or tri-ester, the ester having a weight percent of oxygen from 12 to 45 to decrease the viscosity of a hydratable concentrated surfactant composition.

As used herein, “compositions” with no qualifier are meant to mean the hydratable concentrated surfactant composition and end use composition of this invention. Hydratable, as used herein, means add and/or add and absorb water (i.e., to dilute) even to a composition that has water such as a composition that is initially 30 to 85% by weight water. Skin, as used herein, is meant to include skin on the arms (including underarms), face, feet, neck, chest, hands, legs, buttocks and scalp (including hair). Hydratable concentrated surfactant composition (“hydratable composition”) means a lamellar composition that increases in viscosity when water is added to the composition to thereby produce an isotropic end use composition suitable for topical application. Lamellar, as used herein, means a two-dimensional phase with lipid bilayers separated by water layers, an opaque and cloudy composition. Isotropic means having lipid layers of one dimension and a transparent composition. Transforming from a lamellar to an isotropic phase is confirmed by visual examination of an opaque concentrate becoming a transparent end use composition after the hydratable composition is hydrated. The hydratable composition is one which is suitable to optionally have a viscosity from 0.5 to 1.5 PaS (500 to 1,500 cps). (1 Pa-s is equal to 1000 cps). The end use composition is one suitable to be wiped or washed off, and preferably, washed off with water. The end use composition can be a home care cleaning composition but is preferably a shampoo, make-up wash, facial wash, hand wash or personal care liquid body wash. In an embodiment of the invention, the end use composition can optionally have a viscosity from 6 to 12 PaS (6,000 to 12,000 cps) when a body wash and from 2 to 5 PaS (2,000 to 5,000 cps) when a hand wash. The end use composition may, optionally, comprise medicinal or therapeutic agents, but preferably, is a wash which is cosmetic and non-therapeutic such that the wash removes water soluble and water insoluble soils. In one embodiment of the invention, the end use composition is a home care composition like a table-top or toilet cleaning composition. In another embodiment, the end use composition is a shampoo composition. In still another embodiment, the end use composition is a personal wash composition, and therefore, a liquid body wash. As hereinafter described, the end use composition of the present invention may optionally comprise skin benefit ingredients added thereto such as emollients, vitamins and/or derivatives thereof, resorcinols, retinoic acid 5 precursors, colorants, moisturizers, sunscreens, mixtures thereof or the like. The skin benefit ingredients (or agents) may be water or oil soluble. If used, oil soluble skin benefit agents typically make up to 1.5% by weight of the hydratable composition whereby water soluble skin benefit agents, when used, typically make up to 10% by weight of the hydratable composition of the present invention. The hydratable composition and end use composition typically have a pH from 3.5 to 10. Viscosity, unless noted otherwise, is taken with a Discovery HR-2 Rheometer using sand blasted plates with a 100 micron gap and a shear rate of 4-15 $s^{-1}$. Viscosity is measured at 25° C. Increase in viscosity means the hydratable composition of the present invention will have a starting viscosity that is lower than the final viscosity after water is added and the resulting end use composition is made. The end use composition is made by combining water and hydratable composition and mixing (with moderate shear like stirring, preferably shaking) the same to produce the end use composition having a higher viscosity than the hydratable composition it is made from. In another embodiment, the hydratable composition may be applied directly to, for example, skin of a consumer and when water and shear are applied (like, for example, shearing with the hand and water from a sink or shower) the desired end use composition may be made. As used herein, “substantially free of sulfate” means less than 6.0% by weight of the end use composition, and “substantially free of oil” means less than 0.3% by weight of the end use composition. Structurant means suitable to build viscosity in a hydrated composition. Such a structurant is preferably and optionally used when the anionic surfactant comprises less than 2.0% by weight isethionate. Lamellar phase agent means the agent that induces lipid bilayer formation separated by water layers. The hydratable composition of the present invention when formulated with the ester or esters having a weight percent of oxygen from 12 to 45 surprisingly displayed a viscosity reduction of at least 55%, preferably, 60%, and most preferably, at least 65% less than the same (i.e., same base) hydratable composition that was formulated without the ester or esters. In an embodiment of the invention, the viscosity reduction of the hydratable composition was from 62 to 95% less in comparison to the same hydratable composition that was formulated without such ester or esters. Weight percent oxygen is the percent of oxygen in the ester calculated from the total molecular weight of such ester. The term comprising is meant to encompass the terms consisting essentially of and consisting of. For the avoidance of doubt, and for illustration, the end use composition of this invention comprising surfactant, water and active is meant to include a composition consisting essentially of the same and a composition consisting of the same. All ranges defined are meant to include all ranges subsumed therein. Except in the operating comparative examples, or where otherwise explicitly indicated, all numbers in this description indicating amounts or ratios of materials or conditions and/or physical properties of materials and/or use are to be understood as modified by the word “about”.

DETAILED DESCRIPTION OF THE INVENTION

As to the anionic surfactant, the same typically makes up from 1.0 to 30% by weight of the hydratable composition. In an embodiment of the invention, the anionic surfactant makes up from 2.0 to 25% by weight, and preferably, from to 3.0 to 20% by weight, and most preferably, from 6 to 15% by weight of the hydratable composition. Still in another embodiment, anionic surfactant makes up from 7 to 14% by weight of the hydratable composition. In another embodiment, the anionic surfactant is 1 to 100%, and preferably, from 30 to 100%, and most preferably, from 35 to 100% by weight isethionate, taurate and/or glycinate, based on total weight of anionic surfactant used in the compositions. In still another embodiment, anionic surfactant is 100% isethionate, taurate, glycinate or a mixture thereof.

As to the amphoteric and/or zwitterionic surfactant used in the hydratable composition, the same typically makes up from 1.0 to 45%, and preferably, from 2.0 to 35%, and most preferably, from 12 to 25% by weight of the hydratable composition.

To, for example, aid in hydratable composition lamellar phase stabilization and hydration, a lamellar phase agent like a $C_6$-$C_{14}$ acid or an alcohol and/or amide derivative thereof, is preferably used and typically makes up from 1.0 to 16%, and preferably, from 1.8 to 12%, and most preferably, from 3 to 8% by weight of the hydratable composition. The preferred agent for use is myristic acid, lauric acid and any alcohol or amide derivatives thereof. In a most preferred embodiment, the lamellar phase agent used is lauric acid. In yet another preferred embodiment, the lamellar phase agent makes up from 4.2 to 5.2% by weight of the hydratable concentrated composition.

As to the esters suitable for use in the present invention, the same are limited only to the extent that they aid in the viscosity reduction of the hydratable composition and are suitable for use in and end use composition that is safely applied by and/or topically to a consumer. The esters used are soluble in the hydratable composition of the invention and can be mono-, di-, or tri-esters as well as mixtures thereof. In a preferred embodiment, the esters used in the hydratable composition of the present invention have a weight percent of oxygen from 12 to 45, and preferably, from 13 to 45, and most preferably, from 14 to 45. Such esters often comprise hexyl salicylate, hexyl acetate, diethylhexyl malate, dioctyl maleate, glyceryl caprylate, glycerin triacetate or a mixture thereof. In a most preferred embodiment, the ester employed in the hydratable composition is hexyl salicylate, hexyl acetate, diethylhexyl malate, dioctyl maleate, glyceryl caprylate, glycerin triacetate or a mixture thereof.

Typically, the ester suitable for use makes up from 0.5 to 5.0%, and preferably, from 1.0 to 4.5%, and most preferably, from 2.5 to 3.5% by weight of the hydratable composition. In an especially preferred embodiment, ester makes up from 2.75 to 3.3% by weight of the hydratable composition.

Inorganic salt is an optional but often desired ingredient to aid in composition stabilization. Typical salts may be used like NaCl, KCl, $MgCl_2$, $CaCl_2$), mixtures thereof or the like. Typically, the inorganic salt makes up from 0 to 15%, and preferably, from 1 to 12%, and most preferably, from 0.75 to 4.5% by weight of the hydratable concentrated composition. In an embodiment of the invention, salt makes up from 2.5 to 3.5% by weight of the hydratable concentrated composition.

Structurants, often polymeric viscosity aids, are optionally used as an ingredient in the hydratable composition of the present invention. Illustrative examples of the structurants suitable for use in the invention include esters of polyalkoxylated polyols and fatty acids.

Examples of such structurants include PEG 18 glyceryloleate/cocoate, polyethylene glycol 6000 distearate, INCI name of PEG-150 distearate; PEG 120 methyl glucose dioleate and PEG 120 methylglucose trioleate (Glucomate™ DOE-120 and Glucomate™ VLT made available by Lubrizol); PEG-150 Pentaerythrityl Tetrastearate (Crothix™, Crothix™ Liquid, and Versathix™ made available by Croda); PEG-150 Polyglyceryl-2 Tristerate (Genapol® LT made available by Clariant); PEG/PPG-120/10-Trimethlolpropane Trioleate (Arlypon® TT made available by BASF). The number of hydrophilic polyalkoxylated arms are two for PEG-150 distearate, three for Arlypon® TT, four for Genapol® LT and Crothix™, Crothix™ Liquid, and Versathix™, and five for Glucomate™ DOE-120.

The preferred structurants (classified as high molecular weight ethoxylated fatty acid esters) are PEG 120 methyl glucose dioleate, as well as PEG 150 pentaerythrityl tetrastearate. The structurants used make up from 0.1 to 1.2%, and preferably, from 0.2 to 1.0%, and most preferably, from 0.25 to 0.8% by weight of the hydratable composition. In an embodiment of the invention, the structurant makes up from 0.35 to 0.65% by weight of the hydratable composition. Again, such structurants are preferably and optionally used when the anionic surfactant comprises less than 2.0% by weight isethionate based on total weight of anionic surfactant in the compositions.

In another embodiment of the invention, less than 3.0% by weight sulfate is present in the end use composition of the present invention, preferably less than 1.0% by weight, and most preferably, no (0.0% by weight) sulfate. In the present invention, the hydratable composition should be formulated such that upon dilution, the desired component/ingredient levels (such as sulfate levels) in the end use composition are attained.

As to anionic surfactants suitable for use in the hydratable concentrated surfactant composition and end use composition of the present invention, the anionic surfactant used can include aliphatic sulfonates, such as a primary alkane (e.g., $C_8$-$C_{22}$) sulfonate, primary alkane (e.g., $C_8$-$C_{22}$) disulfonate, $C_8$-$C_{22}$ alkene sulfonate, $C_8$-$C_{22}$ hydroxyalkane sulfonate or alkyl glyceryl ether sulfonate (AGS); or aromatic sulfonates such as alkyl benzene sulfonate. As noted, sulfates, when used, make up less than 6.0% by weight of the end use composition.

The anionic may also include alkyl sulfosuccinates (including mono- and dialkyl, e.g., $C_6$-$C_{22}$ sulfosuccinates); alkyl and acyl taurates (often methyl taurates), alkyl and acyl sarcosinates, sulfoacetates, $C_8$-$C_{22}$ alkyl phosphates and phosphonates, alkyl phosphate esters and alkoxyl alkyl phosphate esters, acyl lactates, $C_8$-$C_{22}$ monoalkyl succinates and maleates, sulphoacetates, alkyl glucosides and acyl isethionates, and the like.

Sulfosuccinates may be monoalkyl sulfosuccinates having the formula:

$$R^1O_2CCH_2CH(SO_3M)CO_2M;$$

and amide-MEA sulfosuccinates of the formula:

$R^1CONHCH_2CH_2O_2CCH_2CH(SO_3M)CO_2M$ wherein $R^1$ ranges from $C_8$-$C_{22}$ alkyl.

Sarcosinates are generally indicated by the formula:

$R^2CON(CH_3)CH_2CO_2M$, wherein $R^2$ ranges from $C_8$-$C_{20}$ alkyl.

Taurates are generally identified by formula:

$$R^3CONR^4CH_2CH_2SO_3M$$

wherein $R^3$ is a $C_8$-$C_{20}$ alkyl, $R^4$ is a $C_1$-$C_4$ alkyl.

M is a solubilizing cation as previously described.

Isethionates suitable for use may include $C_8$-$C_{18}$ acyl isethionates (including those which have a substituted head group such as a Ca alkyl substitution, preferably methyl substitution). These esters are prepared by a reaction between alkali metal isethionate with mixed aliphatic fatty acids having from 6 to 18 carbon atoms and an iodine value of less than 20. Often at least 75% of the mixed fatty acids have from 12 to 18 carbon atoms and up to 25% have from 6 to 10 carbon atoms.

The acyl isethionate that may be used can be an alkoxylated isethionate such as is described in Ilardi et al., U.S. Pat.

No. 5,393,466, entitled "Fatty Acid Esters of Polyalkoxylated isethonic acid; issued Feb. 28, 1995. This compound has the general formula:

$R^5C—O(O)—C(X)H—C(Y)H—(OCH_2—CH_2)_m—SO_3M$ wherein $R^5$ is an alkyl group having 8 to 18 carbons, m is an integer from 1 to 4, X and Y are each independently hydrogen or an alkyl group having 1 to 4 carbons and M is a solubilizing cation as previously described.

In an embodiment of the invention, the anionic surfactant used is sodium cocoyl isethionate, sodium lauroyl isethionate, sodium lauroyl glycinate, sodium cocoyl glycinate, sodium lauroyl glutamate, sodium cocoyl glutamate, sodium methyl lauroyl taurate, sodium methyl cocoyl taurate or a mixture thereof. Such anionic surfactants are commercially available from suppliers like Galaxy Surfactants, Clariant, Sino Lion and Innospec. Sodium methyl lauroyl taurate, sodium lauroyl glycinate, sodium lauroyl isethionate or mixtures thereof are the preferred anionics used in this invention. In an embodiment of the invention, the anionic surfactant of the present invention has less than 2.0% by weight isethionate, and in another embodiment, less than 1.0% by weight isethionate based on total weight of anionic surfactant in the compositions.

Amphoteric surfactants suitable for use in the invention (which depending on pH can be zwitterionic) include sodium acyl amphoacetates, sodium acyl amphopropionates, disodium acyl amphodiacetates and disodium acyl amphodipropionates where the acyl (i.e., alkanoyl group) can comprise a $C_7$-$C_{18}$ alkyl portion. Illustrative examples of the amphoteric surfactants suitable for use include sodium lauroamphoacetate, sodium cocoamphoacetate and mixtures thereof. If present such surfactants make up from 0.01 to 5% and preferably, from 0.1 to 2.5% by weight of the hydratable composition.

As to the zwitterionic surfactants that may be employed in the present invention, such surfactants include at least one acid group. Such an acid group may be a carboxylic or a sulphonic acid group. They often include quaternary nitrogen, and therefore, can be quaternary amino acids. They should generally include an alkyl or alkenyl group of 7 to 18 carbon atoms generally comply with an overall structural formula:

$R^6—[—C(O)—NH(CH_2)_q—]_r—N^+—(R^7—)(R^8)A\text{-}B$ where $R^6$ is alkyl or alkenyl of 7 to 18 carbon atoms; $R^7$ and $R^3$ are each independently alkyl, hydroxyalkyl or carboxyalkyl of 1 to 3 carbon atoms; q is 2 to 4; r is 0 to 1; A is alkylene of 1 to 3 carbon atoms optionally substituted with hydroxyl, and B is $—CO_2—$ or $—SO_3—$.

Suitable zwitterionic surfactants for use in the present invention and within the above general formula include simple betaines of formula:

$R^6—N^+—(R^7)(R^8)CH_2CO_2^-$ and amido betaines of formula:

$R^6—CONH(CH_2)_t—N^+—(R^7)(R^8)CH_2CO_2^-$ where t is 2 or 3.

In both formulae $R^6$, $R^7$ and $R^3$ are as defined previously. $R^6$ may, in particular, be a mixture of $C_{12}$ and $C_{14}$ alkyl groups derived from coconut oil so that at least half, preferably at least three quarters of the groups $R^6$ have 10 to 14 carbon atoms. $R^7$ and $R^3$ are preferably methyl.

Another option is that the zwitterionic surfactant is a sulphobetaine of the formula:

$R^6—N^+—(R^7)(R^8)(CH_2)_3SO_3^-$ or $R^6—CONH(CH_2)_u—N^+—(R^7)(R^8)(CH_2)_3SO_3^-$ where u is 2 or 3, or variants of these in which $—(CH_2)_3SO_3^-$ is replaced by $—CH_2C(OH)(H)CH_2SO_3^-$.

In these formulae, $R^6$, $R^7$ and $R^8$ are as previously defined.

Illustrative examples of the zwitterionic surfactants suitable for use include betaines like cocodimethyl carboxymethyl betaine, cocamidopropyl betaine and laurylamidopropyl betaine. An additional zwitterionic surfactant suitable for use includes cocamidopropyl sultaine. Such surfactants are made commercially available from suppliers like Stepan Company, and it is within the scope of the invention to employ mixtures of the aforementioned surfactants. In a preferred embodiment, the zwitterionic surfactant used in the compositions of this invention is cocamidopropyl betaine.

Zwitterionic surfactants are preferably used and make up from 2 to 28%, and preferably, from 6 to 25%, and most preferably, from 12 to 22% by weight of the hydratable composition. In an embodiment of the invention, zwitterionic surfactant makes up from 16 to 21% by weight of the hydratable concentrate.

Nonionic surfactants may optionally be used in the hydratable composition and end use composition of the present invention. When used, nonionic surfactants are typically used at levels as low as 0.5, 1, 1.5 or 2% by weight and at levels as high as 6, 8, 10 or 12% by weight of the end use composition. The nonionics which may be used include in particular the reaction products of compounds having a hydrophobic group and a reactive hydrogen atom, for example aliphatic alcohols, acids, amides or alkylphenols with alkylene oxides, especially ethylene oxide either alone or with propylene oxide. Specific nonionic surfactant compounds are alkyl ($C_6$-$C_{22}$) phenols ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ethylenediamine. Other nonionic surfactants include long chain tertiary amine oxides, long chain tertiary phosphine oxides, dialkyl sulphoxides, and the like.

In an embodiment of the invention, nonionic surfactants optionally used can include fatty acid/alcohol ethoxylates having the following structures a) $HOCH_2(CH_2)_s(CH_2CH_2O)_v H$ or b) $HOOC(CH_2)_c(CH_2CH_2O)_d H$; where s and v are each independently an integer up to 18; and c and d are each independently an integer from 1 or greater. In an embodiment of the invention, s and v are each independently 6 to 18; c and d are each independently 1 to 30. Other options for nonionic surfactants include those having the formula $HOOC(CH_2)_i—CH{=}CH—(CH_2)_k(CH_2CH_2O)_z H$, where i, k are each independently 5 to 15; and z is 5 to 50. In another embodiment of the invention, i and k are each independently 6 to 12; and z is 15 to 35.

The nonionic may also include a sugar amide, such as a polysaccharide amide. Specifically, the surfactant may be one of the lactobionamides described in U.S. Pat. No. 5,389,279 to Au et al., entitled "Compositions Comprising Nonionic Glycolipid Surfactants issued Feb. 14, 1995; or it may be one of the sugar amides described in U.S. Pat. No. 5,009,814 to Kelkenberg, titled "Use of N-Poly Hydroxyalkyl Fatty Acid Amides as Thickening Agents for Liquid Aqueous Surfactant Systems" issued Apr. 23, 1991.

In an embodiment of the invention, cationic surfactants may optionally be used in the hydratable composition and end use composition of the present invention.

One class of optional cationic surfactants includes heterocyclic ammonium salts such as cetyl or stearyl pyridinium chloride, alkyl amidoethyl pyrrylinodium methyl sulfate, and lapyrium chloride.

Tetra alkyl ammonium salts are another useful class of cationic surfactants suitable for optional use. Examples include cetyl or stearyl trimethyl ammonium chloride or bromide; hydrogenated palm or tallow trimethylammonium halides; behenyl trimethyl ammonium halides or methyl sulfates; decyl isononyl dimethyl ammonium halides; ditallow (or distearyl) dimethyl ammonium halides, and behenyl dimethyl ammonium chloride.

Still other types of cationic surfactants that may be used are the various ethoxylated quaternary amines and ester quats. Examples include PEG-5 stearyl ammonium lactate (e.g., Genamin KSL manufactured by Clariant), PEG-2 coco ammonium chloride, PEG-15 hydrogenated tallow ammonium chloride, PEG 15 stearyl ammonium chloride, dipalmitoyl ethyl methyl ammonium chloride, dipalmitoyl hydroxyethyl methyl sulfate, and strearyl amidopropyl dimethylamine lactate.

Even other useful cationic surfactants suitable for optional use include quaternized hydrolysates of silk, wheat, and keratin proteins, and it is within the scope of the invention to use mixtures of the aforementioned cationic surfactants.

If used, cationic surfactants will make up no more than 1.0% by weight of the hydratable composition. When present, they typically make up from 0.01 to 0.7%, and more typically, from 0.1 to 0.5% by weight of the end use composition, including all ranges subsumed therein.

In an embodiment of this invention, the end use composition of this invention will be substantially free of polymeric quaternary ammonium compounds (including salts of the same). In another embodiment, the end use composition will comprise less than 0.1% by weight polymeric quaternary ammonium compounds. In yet another embodiment, the end use composition comprises less than 0.01% by weight polymeric quaternary ammonium compounds. In even another embodiment, the hydratable composition and end use composition are free of polymeric quaternary ammonium compounds (i.e., 0.0%).

Water makes up from 30 to 85%, preferably 30 to 78%, and preferably, from 35 to 75% by weight of the hydratable composition, and most preferably, from 40 to 70% by weight of the hydratable composition.

The pH of the hydratable composition and end use composition is typically from 3.5 to 10, and preferably, from 4.5 to 9, and most preferably, from 4.7 to 7.5, including all ranges subsumed therein. Adjusters suitable to modify/buffer the pH may be used. Such pH adjusters include triethylamine, NaOH, KOH, $H_2SO_4$, HCl, $C_6H_8O_7$ (i.e., citric acid) or mixtures thereof. The pH adjusters are added at amounts to yield the desired final pH. The pH values may be assessed with commercial instrumentation such as a pH meter made commercially available from Thermo Scientific®. In an embodiment of the invention, the pH of the end use composition is 4.8 to 7, in another embodiment from 4.9 to 6.5, and in yet another embodiment, 5.0 to 6.0.

Optional skin benefit agents suitable for use in this invention are limited only to the extent that they are capable of being topically applied, and suitable to dissolve in the hydratable composition and end use composition at the desired pH.

Illustrative examples of the benefit agents suitable to include in the water portion of the compositions are vitamin $B_2$, niacinamide (vitamin $B_3$), vitamin $B_6$, vitamin C, mixtures thereof or the like. Water soluble derivatives of such vitamins may also be employed. For instance, vitamin C derivatives such as ascorbyl tetraisopalmitate, magnesium ascorbyl phosphate and ascorbyl glycoside may be used alone or in combination with each other. Other water soluble benefit agents suitable for use include 4-ethyl resorcinol, extracts like sage, aloe vera, green tea, grapeseed, thyme, chamomile, yarrow, cucumber, liquorice, rosemary extract or mixtures thereof. Water soluble sunscreens like ensulizole may also be used. Total amount of optional water soluble benefit agents (including mixtures) when present in the invention may range from 0.0 to 10%, preferably from 0.001 to 8%, and most preferably, from 0.01 to 6% by weight, based on total weight of the end use composition.

It is also within the scope of the present invention to optionally include oil (i.e., non-water) soluble benefit agents. The end use composition is substantially free of oil, and preferably, has less than 0.15% by weight oil, and most preferably, no oil (0.0%) where oil is not meant to include any oil from a fragrance. Thus, oil soluble actives or benefit agents are solubilized in the surfactants used. The only limitation with respect to such oil soluble benefit agents are that the same are suitable to provide a benefit when topically applied. The composition has preferably less than 0.15% petrolatum (petroleum jelly), more preferably is free from petrolatum.

Illustrative examples of the types of oil soluble benefit agents that may optionally be used in the compositions of this invention include components like stearic acid, vitamins like Vitamin A, D, E and K (and their oil soluble derivatives), sunscreens like ethylhexylmethoxycinnamate, bis-ethyl hexyloxyphenol methoxyphenol triazine, 2-ethylhexyl-2-cyano-3,3-diphenyl-2-propanoic acid, drometrizole trisiloxane, 3,3,5-trimethyl cyclohexyl 2-hydroxybenzoate, 2-ethylhexyl-2-hydroxybenzoate or mixtures thereof.

Other optional oil soluble benefit agents suitable for use include resorcinols like 4-hexyl resorcinol, 4-phenylethyl resorcinol, 4-cyclopentyl resorcinol, 4-cyclohexyl resorcinol 4-isopropyl resorcinol or a mixture thereof. Also, 5-substituted resorcinols like 4-cyclohexyl-5-methylbenzene-1,3-diol, 4-isopropyl-5-methylbenzene-1,3-diol, mixtures thereof or the like may be used. The 5-substituted resorcinols, and their synthesis are described in commonly assigned U.S. Published Patent Application No. 2016/0000669A1.

Even other oil soluble actives suitable for use include omega-3 fatty acids, omega-6 fatty acids, climbazole, farnesol, ursolic acid, myristic acid, geranyl geraniol, oleyl betaine, cocoyl hydroxyethyl imidazoline, hexanoyl sphingosine, 12-hydroxystearic acid, petroselinic acid, conjugated linoleic acid, terpineol, thymol mixtures thereof or the like.

In an embodiment of the invention, the optional oil soluble benefit agent used is a retinoic acid precursor. In one embodiment of the invention, the retinoic acid precursor is retinol, retinal, retinyl propionate, retinyl palmitate, retinyl acetate or a mixture thereof. Retinyl propionate, retinyl palmitate and mixtures thereof are typically preferred. Additionally, 12-hydroxystearic acid is often preferred for use.

When optional oil soluble active is used in the compositions of the invention, it typically makes up from 0.0 to 1.5%, and preferably, from 0.001 to 1.5%, and most preferably, from 0.05 to 1.2% by weight of the end use composition. In yet another embodiment, oil makes up from 0.1 to 0.5% by weight of the total weight of the end use composition.

Preservatives can desirably be incorporated into the hydratable concentrated surfactant composition and end use composition to protect against the growth of potentially harmful microorganisms. Cosmetic chemists are familiar with appropriate preservatives and routinely choose them to satisfy the preservative challenge test and to provide product stability. Suitable traditional preservatives for use include hydantoin derivatives and propionate salts. Particularly preferred preservatives are iodopropynyl butyl carbamate, phenoxyethanol, sodium benzoate, hydroxyacetophenone, ethylhexylglycerine, hexylene glycol, methyl paraben, propyl paraben, imidazolidinyl urea, sodium dehydroacetate, dimethyl-dimethyl (DMDM) hydantoin and benzyl alcohol and mixtures thereof. Other preservatives suitable for use include sodium dehydroacetate, chlorphenesin and decylene glycol. The preservatives should be selected having regard for the use of the composition and possible incompatibilities between the preservatives and other ingredients in the emulsion. Preservatives are preferably employed in amounts ranging from 0.01% to 2.0% by weight of the total weight of the end use composition (up to 7% by weight of total hydratable concentrated surfactant composition), including all ranges subsumed therein. Also preferred is a preservative system with hydroxyacetophenone alone or in a mixture with other preservatives. Standard emollients, like vicinal diols (e.g., 1,2-hexane diol and/or 1,2-octane diol) may be used with the preservatives. In an embodiment of the invention, the preservative used is sodium benzoate when the pH of the compositions is 7 or under, and preferably, 6 or under.

Thickening agents are optionally suitable for use in the compositions of the present invention. Particularly useful are the polysaccharides. Examples include fibers, starches, natural/synthetic gums and cellulosics. Representative of the starches are chemically modified starches such as sodium hydroxypropyl starch phosphate and aluminum starch octenylsuccinate. Tapioca starch is often preferred, as is maltodextrin. Suitable gums include xanthan, sclerotium, pectin, karaya, arabic, agar, guar (including Acacia senegal guar), carrageenan, alginate and combinations thereof. Suitable cellulosics include hydroxypropyl cellulose, hydroxypropyl methylcellulose, ethylcellulose, sodium carboxy methylcellulose (cellulose gum/carboxymethyl cellulose) and cellulose (e.g. cellulose microfibrils, cellulose nanocrystals or microcrystalline cellulose). Sources of cellulose microfibrils include secondary cell wall materials (e.g. wood pulp, cotton), bacterial cellulose, and primary cell wall materials. Preferably the source of primary cell wall material is selected from parenchymal tissue from fruits, roots, bulbs, tubers, seeds, leaves and combination thereof; more preferably is selected from citrus fruit, tomato fruit, peach fruit, pumpkin fruit, kiwi fruit, apple fruit, mango fruit, sugar beet, beet root, turnip, parsnip, maize, oat, wheat, peas and combinations thereof; and even more preferably is selected from citrus fruit, tomato fruit and combinations thereof. A most preferred source of primary cell wall material is parenchymal tissue from citrus fruit. Citrus fibers, such as those made available by Herbacel® as AQ Plus can also be used as source for cellulose microfibrils. The cellulose sources can be surface modified by any of the known methods including those described in Colloidal Polymer Science, Kalia et al., "Nanofibrillated cellulose: surface modification and potential applications" (2014), Vol 292, Pages 5-31.

Synthetic polymers, in addition to structurants, are yet another class of thickening agents that can optionally be used. This category includes crosslinked polyacrylates such as the Carbomers, polyacrylamides such as Sepigel® 305 and taurate copolymers such as Simulgel® EG and Aristoflex® AVC, the copolymers being identified by respective INCI nomenclature as Sodium Acrylate/Sodium Acryloyldimethyl Taurate and Acryloyl Dimethyltaurate/Vinyl Pyrrolidone Copolymer. Another preferred synthetic polymer suitable for thickening is an acrylate-based polymer made commercially available by Seppic and sold under the name Simulgel INS100. Calcium carbonate, fumed silica, and magnesium-aluminum-silicate may also be used.

The amounts of optional thickening agent, when used, may range from 0.001 to 5%, by weight of the compositions. Maltodextrin, xanthan gum, and carboxymethyl cellulose are the often preferred optional thickening agents.

In an embodiment of the invention and given the compositions, the pH of the compositions are in the acidic range, and therefore, no higher than 7, and preferably, no higher than 6.4. In such compositions, the desired preservative is sodium benzoate and the end use composition is formulated with from 0.01 to 4%, and preferably, from 0.05 to 1.5%, and most preferably, from 0.05 to 0.6% by weight of an acidic active or skin benefit agent. Often preferred acidic actives include alpha hydroxy acids like citric acid, glycolic acid, lactic acid, malic acid, tartaric acid or mixtures thereof. Beta hydroxy acids are also suitable for use and these include salicylic acid, salicylate, sodium salicylate, willow, beta hydroxybutanoic acid, tropic acid trethocanic acid or mixtures thereof. Amino acids are also desirable for use and these include arginine, valine and/or histidine.

Fragrances, fixatives, chelators (like EDTA) and exfoliants may optionally be included in the compositions of the present invention. Each of these substances may range from about 0.03 to about 5%, preferably between 0.1 and 3% by weight of the total weight of the end use composition, including all ranges subsumed therein. To the extent the exfoliants are used, those selected should be of small enough particle size so that they do not impede the performance of any packaging used to dispense the compositions of this invention.

Conventional emulsifiers having an HLB of greater than 8 may optionally be used. Illustrative examples include Tween, 40, 60, 80, polysorbate 20 and mixtures thereof. Typically, emulsifiers for water continuous systems make up from 0.3 to 2.5% by weight of the end use composition. In an embodiment of the invention, the emulsifier used is polysorbate 20 in an amount from 0.35 to 1.25% by weight of the end use composition.

Conventional humectants may optionally be employed as additives in the present invention to assist in moisturizing skin when such end use compositions (i.e., emulsions) are topically applied. These are generally polyhydric alcohol type materials. Typical polyhydric alcohols include glycerol (i.e., glycerine or glycerin), propylene glycol, dipropylene glycol, polypropylene glycol (e.g., PPG-9), polyethylene glycol, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. Most preferred is glycerin, propylene glycol or a mixture thereof. The amount of humectant employed may range anywhere from 0.0 to 15% by weight of the total weight of the compositions. Often, humectant makes up from 0.1 to 10%, and preferably, from 0.1 to 2.5% by weight (most preferably, from 0.2 to 1.5% by weight) of the total weight of the end use composition.

As to the end use compositions of the present invention, the same typically have from 1 to 35%, and preferably, from 2 to 30%, and most preferably, from 3 to 16% by weight total surfactant, based on total weight of the end use composition and including all ranges subsumed therein. In an embodiment of the invention, the end use composition comprises from 7 to 10% by weight total surfactant based on total weight of the end use composition and including all ranges subsumed therein.

The present invention is directed to hydratable concentrated surfactant composition that thickens and thus displays an increase in viscosity when mixed and diluted with water. In an embodiment of the invention, when the weight percent of zwitterionic surfactant to the weight percent of anionic surfactant exceeds 3:1 in the compositions, lamellar phase agent (e.g., lauric acid) should be present at over 15% by weight of the total weight of surfactant in the compositions. Additionally, and in another embodiment of the invention, when the zwitterionic surfactant to anionic surfactant weight ratio is less than 1.5, structuring agent makes up 27% by weight or less of the total weight of surfactant in the compositions. In another embodiment, when the weight percent of zwitterionic surfactant to the weight percent of anionic surfactant exceeds 3:1 in the compositions, lamellar phase agent (e.g., lauric acid) should be present at over 15% by weight of the total weight of surfactant in the compositions and when the zwitterionic surfactant to anionic surfactant weight ratio is less than 1.5, structuring agent makes up 27% by weight or less than the total weight of surfactant in the compositions.

When making hydratable composition of the present invention, the desired ingredients may be mixed with conventional apparatus under moderate shear and atmospheric conditions, with temperature being from 35 to 80° C. Water is added to the hydratable composition to produce the end use composition. Moderate shear such as shaking (or stirring) in a container will yield the end use composition in less than 5 minutes, preferably in less than 3 minutes, and most preferably, in less than 2 minutes. In an embodiment of the invention, end use composition is made in less than 1 minute, even preferably, less than 30 seconds.

Accordingly, the present invention relates in a further aspect to a method to prepare an end use composition, the method comprising the step of diluting a hydratable composition of the present invention with water. Preferably, the composition is diluted at a composition to water weight ratio from 1:1 to 1:10. The hydratable concentrated surfactant composition has a viscosity from 0.025 to 10 PaS (25 to 10,000 cps) and upon dilution the viscosity increases resulting in an end use composition having a viscosity from 1 to 20 PaS (1,000 to 20,000 cps), The viscosity is measured with a Discovery HR-2 Rheometer using sand blasted plates with a 100 micron gap and a shear rate of 4-15 s-1 and at a temperature of 25° C.

The packaging for the compositions typically is not limited as long as hydratable composition can be hydrated and end use composition can be made upon the addition of water. In an embodiment on the invention, the hydratable composition is sold in a pouch (including polyvinyl alcohol sachet) or cartridge that is associated with and inserted in a bottle or canister. The bottle or canister is one which is filled with water and allows for the release of the hydratable composition into the same for mixing with water. Typically, the bottle or canister has a cap with a pump that opens the sachet or canister to release the hydratable composition into the water to make end use composition. Such a hydratable composition unexpectedly yields an end use composition, such as a body wash, with desirable characteristics appreciated by consumers.

The packaging allows for infinite numbers of refilling to invariably reduce plastic waste in the environment.

The hydratable concentrated surfactant composition is preferably packaged in a refill packaging. Preferably, the hydratable concentrated composition is used as a refill-composition. Packaging that includes post-consumer resin is often preferred.

The Examples provided are to facilitate an understanding of the invention. They are not intended to limit the scope of the claims.

Example I

A hydratable concentrated surfactant composition was first made by mixing the ingredients shown in Table I, using moderate shear at a temperature of about 75° C. Ester or esters having the relevant weight percent of oxygen were added to the composition as shown in Table II and Table III, the balance being water.

TABLE I

| Ingredient | (Wt. %) |
|---|---|
| Sodium Hydroxide | 0.9 |
| Cocamidopropyl Betaine | 18.7 |
| Lauric Acid | 6.0 |
| Sodium Cocoyl Isethionate | 3.6 |
| Sodium Methyl Lauroyl Taurate | 10.8 |
| Glycerin | 0.95 |
| Tetrasodium EDTA | 0.05 |
| Phenoxyethanol | 2.96 |
| Water | Balance |
| Ester | See Example II |

TABLE II

| Comparative/ Inventive | Ingredients | Weight Percent of Oxygen (Wt. %) | Inclusion Level (wt. %) | Viscosity Change (%) |
|---|---|---|---|---|
| Comparative | Limonene | 0 | 3 | −48.6 |
| Inventive | Dioctyl Maleate | 19 | 3 | −66.9 |
| Inventive | Diethylhexyl Malate | 22 | 3 | −83.1 |
| Inventive | Hexyl Salicylate | 21 | 3 | −76.4 |
| Inventive | Hexyl Acetate | 22 | 3 | −84.4 |
| Inventive | Diisopropyl Adipate | 28 | 3 | −85.7 |
| Comparative | Propylene Glycol | 42 | 3 | 111.7 |
| Comparative | Glycerin | 52 | 3 | 26.1 |

TABLE III

| Comparative/ Inventive | Material | Weight Percent of Oxygen (Wt. %) | Inclusion Level (Wt. %) | Polysorbate (Wt. %) | Viscosity Change (%) | Final Viscosity (PaS (cps)) |
|---|---|---|---|---|---|---|
| Comparative | Limonene | 0 | 3 | 0.5 | −49.1 | 36.58 (36,580) |
| Comparative | Limonene | 0 | 3 | 0 | −48.6 | 36.94 (36,940) |
| Inventive | Dioctyl Maleate | 19 | 3 | 0.5 | −88.9 | 7.966 (7,966) |
| Inventive | Dioctyl Maleate | 19 | 3 | 0 | −66.8 | 23.8 (23,800) |
| Inventive | Diisopropyl Adipate | 28 | 1.5 | 0.5 | −94.2 | 4.172 (4,172) |
| Inventive | Diethylhexyl Malate | 22 | 1.5 | | | |
| Inventive | Diethylhexyl Malate | 22 | 3 | 0 | −83.0 | 12.18 (12,180) |
| Inventive | Diethylhexyl Malate | 22 | 3 | 0.5 | −76.9 | 16.54 (16,540) |
| Inventive | Hexyl Salicylate | 21 | 3 | 0.5 | −83.4 | 11.91 (11,910) |
| Inventive | Hexyl Salicylate | 21 | 3 | 0 | −76.4 | 16.96 (16,960) |
| Inventive | Hexyl Acetate | 22 | 3 | 0.5 | −85.2 | 10.65 (10,650) |
| Inventive | Hexyl Acetate | 22 | 3 | 0 | −84.4 | 11.21 (11,210) |
| Inventive | Diisopropyl Adipate | 28 | 1.5 | 0.5 | −88.1 | 8.524 (8,524) |
| Inventive | Diethylhexyl Malate | 22 | 1.5 | | | |
| Inventive | Diisopropyl Adipate | 28 | 3 | 1 | −93.4 | 4.756 (4,756) |
| Inventive | Diisopropyl Adipate | 28 | 3 | 0.5 | −89.5 | 7.521 (7,521) |
| Inventive | Diisopropyl Adipate | 28 | 3 | 0 | −85.7 | 10.26 (10,260) |

About 20 mL of each hydratable composition were centrifuged at 5000 RPM for 10 minutes in a conventional centrifuge to remove any air trapped in the composition during preparation, to ensure accurate viscosity measurements. The viscosity measurements were taken of each composition made, measured with a Discovery HR-2 Rheometer using sand blasted plates with a 100 micron gap and a shear rate of 4-15 s-1. Viscosity is measured at 25° C.

As can be seen from the data generated, the hydratable compositions made according to this invention displayed a significant reduction in viscosity, and therefore, were surprisingly much easier to pour and dilute in comparison to compositions that that did not contain the ester or esters having the relevant weight percent of oxygen.

Additionally, trained panelists added water to the hydratable compositions made according to this invention (3 parts water to 1 part hydratable composition) to make end use body wash composition. Such body wash compositions where prepared in less than one (1) minute with agitation and they surprisingly thickened (increased in viscosity) when combined with water.

The hydratable compositions were opaque (lamellar) and the end use compositions were surprisingly thicker yet transparent (isotropic) and free of any particulate after making.

Example II

The hydratable composition in this Example was made by adding 3% by weight glycerin triacetate (weight percent oxygen 33) to the composition of Example I. The viscosity reduction observed in the composition was unexpectedly −82%, with a final composition viscosity of 12,896.5 CPS.

What is claimed is:

1. A hydratable concentrated surfactant composition comprising:

a) an anionic surfactant comprising sodium cocoyl isethionate, sodium lauroyl isethionate, sodium lauroyl glycinate, sodium cocoyl glycinate, sodium methyl lauroyl taurate, sodium methyl cocoyl taurate or a mixture thereof;

b) zwitterionic surfactant comprising cocamidopropyl betaine;

c) from 1 to 16% by weight $C_6$-$C_{14}$ acid, or an alcohol, or amide derivative thereof, or mixture thereof;

d) from 30 to 85% by weight water, and e) from 0.5 to 5% by weight of an ester comprising at least one of hexyl acetate, hexyl salicylate, dioctyl malate, diethylhexyl malate, diisopropyl adipate, glyceryl caprylate, glycerin triacetate, diethyl hexyl sebacate, wherein the hydratable concentrated surfactant composition is substantially free of oil and sulfate-based surfactant.

2. The hydratable concentrated surfactant composition according to claim 1, wherein the anionic surfactant comprises sodium lauroyl isethionate, sodium cocoyl isethionate or a mixture thereof, and sodium methyl lauroyl taurate.

3. The hydratable concentrated surfactant composition according to claim 1 wherein the anionic surfactant comprises sodium methyl lauroyl taurate, and sodium lauroyl isethionate, sodium cocoyl isethionate or a mixture thereof and sodium benzoate, phenoxyethanol or a mixture.

4. The hydratable concentrated surfactant composition according to claim 1 wherein the anionic surfactant comprises sodium lauroyl glycinate, sodium cocoyl glycinate or a mixture thereof.

5. The hydratable concentrated surfactant composition according to claim 1 wherein the anionic surfactant comprises sodium cocoyl isethionate, sodium lauroyl isethionate or a mixture thereof.

6. The hydratable concentrated surfactant composition according to claim 1 wherein the composition further comprises a resorcinol, niacinamide, 12-hydroxystearic acid or a mixture thereof.

7. A method for making a wash composition comprising the steps of:

a) combining the hydratable concentrated surfactant composition according to claim 1 with water to produce a water and hydratable composition mix;

b) agitating and/or shearing the mix; and c) producing the wash composition.

8. The method according to claim 7 wherein the wash composition has a pH less than 7 and a viscosity from 1,000 to 20,000 cps.

9. The method composition according to claim 7 wherein the wash composition further comprises a structurant that comprises pentaerythritol tetrastearate.

10. The method according to claim 7 wherein the wash composition is preserved with sodium benzoate.

11. The method composition according to claim 7 wherein the ester is of hexyl salicylate, hexyl acetate, diethylhexyl malate, dioctyl maleate, diisopropyl adipate, glyceryl caprylate, glycerin triacetate, diethyl hexyl sebacate or a mixture thereof.

12. The method according to claim 8 wherein the anionic surfactant comprises sodium methyl lauryl taurate and sodium cocoyl isethionate, and the zwitterionic surfactant comprises cocamidopropyl betaine.

13. The method according to claim 8 wherein the composition further comprises phenoxyethanol.

14. The method according to claim 8 wherein the composition further comprises vitamin B2, niacinamide, vitamin B6, vitamin C, ascorbyl tetraisopalmitate, magnesium ascorbyl phosphate, ascorbyl glycoside, 4-ethyl resorcinol, sage, aloe vera, green tea, grapeseed, thyme, chamomile, yarrow, cucumber, liquorice, rosemary extract, ensulizole, or a mixture thereof.

15. The hydratable concentrated surfactant composition according to claim 1 wherein the composition is lamellar, and increases in viscosity and is an isotropic wash composition after being diluted with water.

16. The hydratable concentrated surfactant composition according to claim 1 wherein the composition further comprises glycerin and lauric acid.

17. The hydratable concentrated surfactant composition according to claim 1 wherein the ester is hexyl acetate, hexyl salicylate, dioctyl malate, diethylhexyl malate, diisopropyl adipate or a mixture thereof.

18. The hydratable concentrated surfactant composition according to claim 1 wherein the composition further comprises vitamin B2, vitamin B6, vitamin C, ascorbyl tetraisopalmitate, magnesium ascorbyl phosphate, ascorbyl glycoside, 4-ethyl resorcinol, 4-hexyl resorcinol, sage, aloe vera, green tea, grapeseed, thyme, chamomile, yarrow, cucumber, liquorice, rosemary extract, ensulizole, or a mixture thereof.

19. The hydratable concentrated surfactant composition according to claim 1 wherein the composition further comprises sodium benzoate, phenoxyethanol or a mixture thereof.

20. The hydratable concentrated surfactant composition according to claim 1 wherein the composition does comprise $C_6$-$C_{14}$ acid and the acid comprises lauric acid.

* * * * *